(12) United States Patent
Stiefel

(10) Patent No.: US 9,277,761 B2
(45) Date of Patent: Mar. 8, 2016

(54) NUTRITION TRACE ELEMENT COMPOSITION

(75) Inventor: Thomas Stiefel, Stuttgart (DE)

(73) Assignee: Biosyn Arzneimittel GmbH, Fellbach (DE)

( * ) Notice: Subject to any disclaimer, the term of this patent is extended or adjusted under 35 U.S.C. 154(b) by 1958 days.

(21) Appl. No.: 10/576,813

(22) PCT Filed: Oct. 25, 2004

(86) PCT No.: PCT/EP2004/012040
§ 371 (c)(1),
(2), (4) Date: Dec. 4, 2006

(87) PCT Pub. No.: WO2005/039604
PCT Pub. Date: May 6, 2005

(65) Prior Publication Data
US 2007/0178192 A1    Aug. 2, 2007

(30) Foreign Application Priority Data

Oct. 24, 2003   (DE) .................................. 103 49 585

(51) Int. Cl.
| | |
|---|---|
| *A61K 33/18* | (2006.01) |
| *A23L 1/304* | (2006.01) |
| *A61K 33/04* | (2006.01) |
| *A61K 33/16* | (2006.01) |
| *A61K 33/24* | (2006.01) |
| *A61K 33/26* | (2006.01) |
| *A61K 33/30* | (2006.01) |

(52) U.S. Cl.
CPC .................. *A23L 1/304* (2013.01); *A61K 33/04* (2013.01); *A61K 33/16* (2013.01); *A61K 33/18* (2013.01); *A61K 33/24* (2013.01); *A61K 33/26* (2013.01); *A61K 33/30* (2013.01); *A23V 2002/00* (2013.01)

(58) Field of Classification Search
USPC ............................................................ 426/72
See application file for complete search history.

(56) References Cited

U.S. PATENT DOCUMENTS

| 6,391,332 | B1 | 5/2002 | Somerville et al. | |
|---|---|---|---|---|
| 6,423,349 | B1 * | 7/2002 | Sherratt et al. | ................ 424/630 |
| 6,660,293 | B2 * | 12/2003 | Giordano et al. | ............. 424/439 |
| 2003/0008016 | A1 | 1/2003 | Crum et al. | |
| 2003/0161863 | A1 | 8/2003 | Ballevre et al. | |

FOREIGN PATENT DOCUMENTS

| DE | 19755367 C2 | 3/2001 |
|---|---|---|
| DE | 10057290 A1 | 6/2002 |
| DE | 10151764 A1 | 5/2003 |
| WO | WO 98/46090 | 10/1998 |

OTHER PUBLICATIONS

Thomson et al. "On supplementing the selenium intake of New Zealanders, 1. Short experiments with large doses of selnite or selenomethionine" in Br. J. Nutr. (1978), 39, p. 579-587.*
Frankel, Daniel A., "Supplementation of Trace Elements in Parenteral Nutrition: Rationale and Recommendations," *Nutrition Research*, 13, 583-593 (1993).
Herrmann, H.J. et al., "Mikronahrstoffe in Der Parenterale Ernahrung: Winzlinge Mit Wirkun Mikronahrstoffe-Funktionen und Interaktione," *Journal fur Ernahrungsmedizin*, 30-32 (2003).
"Substrate der Parenterale Ernahrung," www.medinal.de (2004).
Food and Nutrition Board of the IOM (ed.), *Selenium, In: Dietary Reference Intakes for Vitamin C, Vitamin E, Selenium, and Carotenoids*, National Academy Press (2000), pp. 284-324.

* cited by examiner

*Primary Examiner* — Elizabeth Gwartney
(74) *Attorney, Agent, or Firm* — Leydig, Voit & Mayer, Ltd.

(57) ABSTRACT

The present invention relates to a composition with trace elements for nutrition. The composition is characterized by an increased content of selenium and/or zinc as a trace element.

5 Claims, No Drawings

NUTRITION TRACE ELEMENT COMPOSITION

This application is the U.S. national phase of International Patent Application PCT/EP2004/012040, filed on Oct. 25, 2004, which claims priority to German Patent Application No. 103 49 585.1, filed Oct. 24, 2003, all of which are hereby incorporated by reference.

The present invention relates to a composition with trace elements for nutrition.

Commercially, electrolyte concentrates are understood as such "Nutrition Trace Element Compositions". For example, they are added to infusion solutions in the Red List as a supplement.

In the invention under consideration, the term should be considered as defined to that effect, i.e., "Nutrition Trace Element Compositions" contain electrolyte concentrates exclusively.

Parenteral nutrition is a special form of the administration of nutrients and liquids. It differs from normal oral food ingestion in that the substances reach the organism via an artificially created venous access by means of infusion. The entire digestive tract is bypassed in this way. The indication for intravenous feeding of nutrients always exists when ingestion of nourishment administered orally via the digestive tract is not possible, not desired or too dangerous. In general, parenteral nutrition is used when there are considerable impairments in digestion and resorption, as well as in the framework of intensive care medicine. Complete parenteral nutrition should supply the same nutrients as normal enteral nourishment: carbohydrates, fats, proteins, vitamins, electrolytes, water and also trace elements.

For a long time, artificial nutrition of the ill was only possible orally. The tube technique is said to have been used for the first time in the $16^{th}$ century. The basis for infusion therapy was provided by insights into the body's circulation, which was described in 1628 by the British physician W. Harvey. In the following centuries, there was only slow progress in the infusion technique. For example, attempts to infuse cholera patients with milk failed. The breakthrough in parenteral nutrition came with the development of sterilisation and suitable infusion solutions. Common salt and sugar solutions began to be used at the end of the $19^{th}$ century. The first amino acid infusion was done by Elman in 1937. The first success in developing a safe and utilisable fat emulsion for clinical use was not achieved until 1961. The administration of macro elements and especially trace elements was not taken into consideration for a long time.

Trace elements are important for maintaining physical and mental capabilities. As structural and/or functional constituents of numerous metalloproteins (copper, zinc), enzymes (selenium), hormones (iodine) or vitamins (cobalt), trace elements are involved in many metabolic processes.

Before the introduction of the intravenous provision of nutrients in clinical medicine, trace element deficits affected only population groups in geological areas with deficiencies. With the exception of the classic iodine deficiency, clinical deficiencies almost never arose in Europe and America because of the geochemical and nutrition-related circumstances. Not until the use of parenteral nutrition were there isolated deficiency symptoms in western countries as the result of insufficient administration of trace elements.

A deficiency of trace elements impairs the optimal development of important physiological processes in the body. Trace element deficiency develops in several stages under parenteral nutrition. When there is insufficient administration, the organism falls back on endogenous stores of trace elements. As a result of the emptying of these stores, the deficiency first becomes noticeable through non-specific manifestations, which develop from specific metabolic disorders all the way to the characteristic symptoms of deficiency for each trace element. The classic symptoms of deficiency are reversible in early stages. If substitution is not provided, however, they can cross over into irreversible metabolic disorders, which can even be potentially lethal in a later stage.

Optimal trace element supplementation consequently represents an important component in the framework of artificial nutrition therapy. The emphasis here is on prevention of metabolic disorders which are due to the infusion therapy itself. An additional objective behind an adequate provision of trace elements is to remedy an already existing deficiency and to help the patient to a higher quality of life.

Disorders caused by a trace element deficiency are normally ascertained by means of lowered trace element concentrations in the blood, from which, however, the nutritional-physiological trace element status can be only conditionally inferred. More recent recommendations are increasingly based on losses of activity in trace element-dependent enzymes and on changed metabolic processes in which trace elements are involved. The necessary diagnostic methods are largely lacking in this area. Established requirements that are based on biochemical parameters are available for only a few trace elements at this time. Analytical methods for some rare trace elements are also not available at all clinics. Consequently, the blood levels of the individual trace elements will continue to be used for orientation in determining the trace element status (Gramm et al., 1992).

Which trace elements are seen as essential for humans depends on the latest state of the scientific knowledge. Today the trace elements chromium, iron, fluorine, iodine, copper, manganese, molybdenum, selenium and zinc are considered essential, along with cobalt as a constituent of vitamin $B_{12}$. Recently, the view that additional trace elements—tin, silicon, vanadium, arsenic, lead, aluminium, lithium, cadmium and boron—can also be classified as essential is under discussion. The biological functions of these trace elements and, above all, their essential nature for humans, have not been fully researched yet, however, so that no reliable statements can be made about the requirement yet. The toxic effects of these elements are still in the foreground.

Useful administration of trace elements presumes knowledge of the intravenous requirements for the essential trace elements. While the daily requirements for a healthy person, taking into consideration the circumstances of the individual's life (pregnancy, growth phases, competitive athlete), are largely known, it is difficult to give a recommendation for sick persons. There are several reasons for this.

1. Recommendations for parenteral administration of trace elements are based on the recommendations for oral administration and are corrected by the respective intestinal resorption rate. But even the values for oral administration are made on a weak foundation to some extent, because useable long-term balance studies with generally recognised analytical methods are available only in isolated cases.

2. The required quantity of trace elements always depends on the individual and the biological situation (illness, stress), and is, at the same time, always related to metabolism. Because the main function of the trace elements lies in the fact that they function as co-factors or prosthetic groups for a number of enzymes, the requirement fluctuates, depending on the changes in the enzyme and protein pattern and the metabolic activity during an illness. As the energy turnover increases, the trace element turnover increases, for example, the zinc requirement when carbohydrates are administered.

3. Losses in secretions, drainage fluids and diarrhoea must also be expected in some patients, but the exact level is not known precisely.
4. Moreover, only approximations are known for the resorption rates for the individual elements. They can range between 1 and 90%, and depend on the supply and metabolism. Knowledge of these data is a requirement for transferring the oral recommendations to parenteral administration, however.
5. Special studies of the trace element requirements during parenteral nutrition or during conditions in various illnesses are practically non-existent.

The following table lists the nine essential trace elements, their functions, the possible symptoms of deficiency and the oral dose recommendations from the Deutsche Gesellschaft für Ernährung (DGE—Germany Society for Nutrition) for the healthy adult (DGE2000).

nutrition. The preparation Tracutil® is a trace element solution for parenteral nutrition from B. Braun Melsungen AG. The above-mentioned trace elements are contained in Tracutil®.

Today the trace elements chromium, iron, fluorine, iodine, copper, manganese, molybdenum, selenium and zinc are considered essential, along with cobalt as a constituent of vitamin $B_{12}$. These trace elements should also be administered during parenteral nutrition.

The trace elements cobalt, copper, manganese and zinc are administered by the preparations Inzolen HK and Inzolen® sine NaCl, as are the macro elements chloride, potassium, magnesium and sodium.

The selenium requirement should be covered by administration of Selenase® and an increased requirement for zinc by administration of Unizink®.

The combined administration of macro and trace elements in one solution—as in this case with the preparations Inzolen HK, Inzolen® sine NaCL—and the orientation of the supplementation on the potassium level has proven to be adverse. Furthermore, sporadic use of Selenase® and Unizink® could not guarantee optimal provision of selenium and zinc for the patients.

TABLE 1

Essential Trace Elements

| Element | Function | Symptoms of deficiency | Recommended oral dose |
| --- | --- | --- | --- |
| Chromium | Involved in carbohydrate metabolism, improvement of glucose tolerance | Impaired glucose utilisation, weight loss, encephalopathy | 30-100 µg/d |
| Iron | Constituent of oxygen-transmitting active groups (haemoglobin, myoglobin) | Iron-deficiency anaemia, increased susceptibility to infection, impaired physical capacity | 10-15 mg/d |
| Fluorine | Bone and tooth formation, caries prophylaxis | Caries | 3.1-3.8 mg/d |
| Iodine | Constituent of the thyroid hormones | Hypothyroidism, goitre | 180-200 µg/d |
| Copper | Constituent of enzymes involved in the redox processes, important in iron metabolism, involved in the synthesis of collagen and elastin | Hypochromic microcytic anaemia, leukocytopenia, granulocytopenia, bone fractures, vessel ruptures, aneurysms, neurologica disturbances | 1.0-1.5 mg/d |
| Manganese | Constituent of numerous metalloenzymes, activation of other enzymes | Not observed in humans; in other species: growth disturbances, impaired fat and carbohydrate metabolism | 2.0-5.0 mg/d |
| Molybdenum | Constituent of several enzymes | Not known in humans | 50-100 µg/d |
| Selenium | Anti-oxidative effect, inactivation of free radicals, protection of membranes, also anti-carcinogenic effect and strengthening of immune system | Cardiomyopathy, myopathy of the skeletal muscles, atrophy of muscle fibres, lowered T-lymphocyte activity, erythrocytic macrocytosis, haemolysis tendency | 30-70 µg/d |
| Zinc | Constituent of numerous enzymes, important for healing wounds, in nucleic metabolism, for storing insulin, involved in the transport of carbon dioxide in the blood | Cessation of growth, weight loss, impaired healing of wounds, therapy-resistant diarrhoeas, dermatitis, depression of the cellular immune response, increased susceptibility to infection, neurological events | 7-10 mg/d |

According to contemporary knowledge, the trace elements chromium, iron, fluorine, iodine, copper, manganese, molybdenum, selenium and zinc should be substituted in parenteral Additional commercial trace element preparations are "Decan®" and "Mikro+Pediatric™", which have various disadvantages, however, as illustrated in Tables 2 and 3.

TABLE 2

| | | Micro+6 Pediatric ™ | | Recommendations, parenteral dose/day American Medical Association 1979, 1984; Fleming 1989; Berger 1995; Shenkin 1995 | |
|---|---|---|---|---|---|
| $Fe^{2+}$ | 55.8 | 0.00 mg | 0.00 μmol | 1.2 mg | 21.49 μmol |
| $Zn^{2+}$ | 65.4 | 3.00 mg | 45.9 μmol | 2.4–15 mg 2.5–5 | 36.70 229.39 μmol |
| $Mn^{2+}$ | 54.9 | 0.10 mg | 1.82 μmol | 0.15–0.8 mg 0.06–0.1 | 2.73 14.56 μmol |
| $Cu^{2+}$ | 63.6 | 0.40 mg | 6.29 μmol | 0.3–1.6 mg 0.3–0.5 | 4.72 25.18 μmol |
| $F^-$ | 19 | 0.00 mg | 0.00 μmol | 0.95 mg | 50.03 μmol |
| $J^-$ | 127 | 0.06 mg | 0.47 μmol | 0.131 mg | 1.03 μmol |
| $Cr^{3+}$ | 52 | 0.04 mg | 0.77 μmol | 0.01–0.03 mg 0.01–0.015 | 0.19 0.58 μmol |
| $Se^{4+}$ | 79 | 0.02 mg | 0.25 μmol | 0.03–0.5 mg | 0.38 6.33 μmol |
| $Mo^{4+}$ | 95.9 | 0.00 mg | 0.00 μmol | 0.019–0.2 mg | 0.20 2.08 μmol |

$Fe^{2+}$: While "zero" does not correspond to the recommendations, more recent studies (among others, Mette Berger 2004; ESICM Berlin) show, however, that administration of iron has no advantages, but rather contributes to radical stress.

$Zn^{2+}$: 3 mg corresponds to the previous dose recommendations, however various studies indicate that when there is an existing zinc deficiency, 30–40 mg must be provided daily to remedy it (e.g., Hackl 1992).

$Mn^{2+}$: 0.1 mg corresponds to the minimum recommendations. According to the literature, higher manganese concentrations should be considered dangerous. The primary complication is the depositing of manganese in the basal ganglia, which can be connected to Parkinson-like symptoms and which is probably irreversible. For this reason, the manganese level should be routinely determined (Shenkin 2001).

$Cu^{2+}$: 0.4 mg corresponds to the minimum recommendations. From the literature, it is known that the quantities of copper in all blood fractions are connected to one another and their copper contents are not (directly) dependent on alimentary administration, but instead are dependent on such factors as daily rhythm, sex, age, hormone status, inflammatory processes, and many more. Consequently, there is a constant exchange between the intracellular and extracellular areas (Rükgauer and Kruse-Jarres 2000).

$F^-$: "Zero" does not correspond to the recommendations; more recent studies (biosyn) show, however, that usually the tendency is rather to administer too much fluorine via anaesthesia containing fluorine, so that no additional administration of F would be necessary in the case of short-term parenteral nutrition. All the same, it is maintained that only inorganic fluorine compounds are physiologically effective (Heseker 1999) and consequently the organic cannot be considered as added fluorine.

$J^-$: 0.06 mg corresponds to approximately half of the recommended dose; because the iodine supply of the patients is usually supernormal due to contrast and disinfection agents containing iodine, an iodine deficiency should consequently not be possible; the question that remains, however, is whether administration of iodine in this way should be recommended at all: If too much iodine is administered, there is a risk that there will be an acute rise in the thyroid hormones in patients with prior iodine-deficient nourishment.(A normally functioning thyroid gland with a sufficient iodine supply is capable of inhibiting the adsorption and formation of organic iodine compounds (Wolff-Chaikoff effect).)

$Cr^{3+}$: 0.04 mg is somewhat more than the recommendations; possibly, however, more recent insights are taken into account (Berger 2004), which indicate that administration of 0.04 mg reduces glycaemia and insulin anaemia. In other studies (biosyn), however, it was found that as a rule there is no inadequate provision of Cr, because many solutions are contaminated with Cr (Shenkin 2001).

$Se^{4+}$: 0.02 mg is even less than the dose recommendations, however numerous studies (e.g. biosyn) show that daily administration of 1 mg is advantageous, and does not lead to supernormal blood levels.

$Mo^{4+}$: "Zero" does not correspond to the dose recommendations, but the data on Mo found in the literature is often contradictory, which may be due to difficulties in making measurements; for example, high levels could even be generated by contamination when the blood sample is drawn with steel cannulas (Versieck 1983).

TABLE 3

| | | Baxter Decan ®: | | Recommendations, parenteral dose/day American Medical Association 1979, 1984; Fleming 1989; Berger 1995; Shenkin 1995 | |
|---|---|---|---|---|---|
| $Fe^{2+}$ | 55.8 | 1.00 mg | 17.90 μmol | 1.2 mg | 21.49 μmol |
| $Zn^{2+}$ | 65.4 | 10.00 mg | 153.00 μmol | 2.4–15 mg 2.5–5 | 36.70 229.39 μmol |
| $Mn^{2+}$ | 54.9 | 0.20 mg | 3.64 μmol | 0.15–0.8 mg 0.06–0.1 | 2.73 14.56 μmol |
| $Cu^{2+}$ | 63.6 | 0.48 mg | 7.55 μmol | 0.3–1.6 mg 0.3–0.5 | 4.72 25.18 μmol |
| $F^-$ | 19 | 1.45 mg | 76.30 μmol | 0.95 mg | 50.03 μmol |
| $J^-$ | 127 | 0.0015 mg | 0.012 μmol | 0.131 mg | 1.03 μmol |
| $Cr^{3+}$ | 52 | 0.015 mg | 0.289 μmol | 0.01–0.03 mg 0.01–0.015 | 0.19 0.58 μmol |
| $Se^{4+}$ | 79 | 0.07 mg | 0.887 μmol | 0.03–0.5 mg | 0.38 6.33 μmol |

TABLE 3-continued

| | Baxter Decan ®: | | | Recommendations, parenteral dose/day American Medical Association 1979, 1984; Fleming 1989; Berger 1995; Shenkin 1995 | |
|---|---|---|---|---|---|
| $Mo^{4+}$ | 95.9 | 0.025 mg | 0.261 µmol | 0.019–0.2 mg | 0.20 2.08 µmol |
| Co | 58.9 | 0.074 mg | 1.261 µmol | — | — — — |

$Fe^{2+}$: 1 mg is slightly less than the recommendations; more recent studies (among others, Mette Berger 2004; ESICM Berlin) show, however, that administration of iron has no advantages, but rather contributes to radical stress.
$Zn^{2+}$: 10 mg corresponds to previous recommendations, but is indeed very high in comparison to other solutions. Various studies indicate that when there is an existing zinc deficiency, 30–40 mg must be provided daily to remedy it (e.g., Hackl 1992).
$Mn^{2+}$: 0.2 mg corresponds to the recommendations. According to the literature, higher manganese concentrations should be considered dangerous. The primary complication is the depositing of manganese in the basal ganglia, which can be connected to Parkinson-like symptoms and which is probably irreversible. For this reason, the manganese level should be routinely determined (Shenkin 2001).
$Cu^{2+}$: 0.48 mg corresponds to the recommendations. From the literature, it is known that the quantities of copper in all blood fractions are connected to one another and their copper contents are not (directly) dependent on the alimentary administration, but instead are dependent on such factors as daily rhythm, sex, age, hormone status, inflammatory processes, and many more. Consequently, there is a constantexchange between the intracellular and extracellular areas (Rükgauer and Kruse-Jarres 2000).
$F^-$: 1.45 mg is more than the recommendations; more recent studies (biosyn) show, however, that usually the tendency is rather to administer too much fluorine via anaesthesia containing fluorine, so that no additional administration of F would be necessary in the case of short-term parenteral nutrition. All the same, it is maintained that only the inorganic fluorine compounds are physiologically effective(Heseker 1999) and consequently the organic cannot be considered as added fluorine.
$J^-$: 0.0015 mg corresponds to roughly 1/90 of the recommended dose; because the iodine supply of the patients is usually supernormal due to contrast and disinfection agents containing iodine, an iodine deficiency should consequently not be possible; the question that remains, however, is whether administration of iodine in this way should be recommended at all: If too much iodine is administered,there is a risk that there will be an acute rise in the thyroid hormones in patients with prior iodine-deficientnourishment. (A normally functioning thyroid gland with a sufficient iodine supply is capable of stemming the adsorption and formation of organic iodine compounds (Wolff-Chaikoff effect).).
$Cr^{3+}$: 0.015 mg corresponds to the minimum recommendations; possibly, however, this is against the background of the more recent insights (Berger 2004), which indicate that administration of 0.04 mg reduces glycaemia and insulin anaemia. In other studies (biosyn), however, it was found that as a rule there is no inadequate provision of Cr, because many solutions are contaminated with Cr (Shenkin 2001).
$Se^{4+}$: 0.07 mg is within the dose recommendations; however numerous studies (e.g. biosyn) show that daily administration of 1 mg is advantageous, and does not lead to supernormal blood levels.
$Mo^{4+}$: 0.025 mg is slightly more than the dose recommendations; but the data on Mo found in the literature is often contradictory, which may be due to difficulties in making measurements; for example, high levels could even be generated by contamination when the blood sample is drawn with steel cannulas (Versieck 1983).
Co: Separate administration of cobalt is not recommended, because it is administered via cobalamin = vitamin B12.

Therefore, it can be concluded that the trace element substitution that is routinely administered at this time leads to a disbalance between macro elements and trace elements in the blood. By using the Inzolen preparations, extreme overdosages of macro elements and trace elements, such as magnesium, copper and manganese, for example, occurred. In contrast to this, iron, selenium and zinc were not administered, or not administered in sufficient levels. The most crucial disadvantage of the Inzolen preparation is therefore that macro elements and trace elements cannot be dispensed separately. On the one hand, the clinical routine does not allow for establishing each trace element in the blood daily for each patient, and then aligning the trace element supplementation with the results. On the other hand, macro elements and trace elements should be administered in a manner that is as individual as possible. Therefore, the goal should be to develop a trace element solution that is put together in such a way that it is optimal for intensive care patients, particularly for sepsis patients, with this solution guaranteeing the basic supply of the above-mentioned essential elements and doing justice to the increased need for selenium and/or zinc.

The present invention takes as its basis the technical problem of specifying a nutrition composition containing trace elements that covers the actual requirements of the person receiving nourishment for the trace elements selenium and zinc better than is possible with the state-of-the-art compositions.

This problem is solved according to the invention by a nutrition composition containing trace elements; this composition is characterised in that a daily dosage of this composition provides 0.04 mg-2.0 mg of selenium and/or 10.0 mg-100 mg of zinc as trace element(s).

Furthermore, the composition according to the invention in a preferred embodiment differs from the state of the art in that in the composition according to the invention, no iron is contained as a trace element.

The composition according to the invention contains a considerably higher concentration of zinc and/or selenium (with respect to the other trace elements) than do the state-of-the-art preparations. While the ratio of the concentration of selenium to chromium lies in the range of 2:1 in the state of the art, this is preferably at least 5:1, particularly preferably at least 10:1, in the compositions according to the invention. For zinc, the ratio Zn:Cr in the state of the art is G.300:1, while in the present invention the ratio is preferably at least 1000:1, particularly preferably at least 3000:1.

Iron deficiency is particularly caused by high losses of blood caused by trauma or surgery, and must be balanced out by a blood transfusion in particular. Because bacteria need free iron to grow, the drop in the serum iron during infections and traumas as a result of an increase in the iron storage (ferritin) induced by cytokine represents a component in the non-specific immune defence. For these reasons, substitution of free iron should be refrained from in the acute phase and when there are infections.

In a further preferred embodiment, the composition according to the invention exists as an infusion solution.

The selenium and/or zinc contained in the composition can exist in various forms. Both inorganic and organic selenium compounds can be used as the substances containing selenium. Among the inorganic selenium compounds are, for example, selenite and selenate, whereby sodium selenite is particularly preferred. Among the organic selenium compounds are selenomethionine, selenocysteine as well as compounds with the following general formula: $R_1—(Se)_n—R_2$, where n is a whole number from 1-8; $R_1$ and $R_2$ can be the same or different, and represent either hydrogen or an alkyl group with 4-12 carbon atoms, whereby the alkyl groups can be substituted for by at least one carboxyl group.

Organic and inorganic compounds can be used as the compounds containing zinc. Among the organic zinc compounds are, for example, the Zn salts of amino acids such as Zn aspartate, for example. Zinc chloride is preferred as an inorganic compound. In addition to the trace elements, the composition preferably contains water for injection purposes, and possibly hydrochloric acid.

In a further preferred embodiment, the composition according to the invention exists as an infusion solution that is suitable for parenteral administration.

In a further preferred embodiment, the composition is provided as a concentrate, which holds 0.004 mg/ml-0.2 mg/ml of selenium and/or 1.0 mg/ml-10 mg/ml of zinc. This concentrate is diluted, e.g., with a compatible infusion solution, before being administered, whereby the concentrate is diluted approximately 1:10 to 1:50 with the compatible infusion solution.

In a further preferred embodiment, the composition contains further trace elements, which are selected from among chromium, copper, fluorine, iodine, manganese and molybdenum. Preferably the composition contains each of these additional trace elements, whereby the concentrations of these trace elements correspond to the state of the art, as, for example, in the commercially available preparation Tracutil®.

In a further preferred embodiment, the composition according to the invention is formulated as an infusion solution, which is preferably formulated as a 10-ml administration unit. Preferably, each administration unit is provided in the form of an ampoule for injection purposes.

The composition according to the invention is preferably used as nutrition for intensive care patients. A daily dose of selenium in the range of 0.04 mg-2.0 mg and a daily dose of zinc in the range of 10 mg-100 mg are administered. Each of these statements refers to the amount of selenium or zinc, so that when corresponding selenium or zinc compounds are used, a correspondingly higher amount must be administered. Consequently, for example, 1 mg of selenium corresponds to the amount of 3.331 mg of sodium selenite×5 $H_2O$. Correspondingly, to administer 30 mg of zinc, 62.542 mg of zinc chloride must be administered.

Intensive care patients are, for example, identified by the following parameters: imminent cardiovascular arrest, respiratory insufficiency and/or coma; additional criteria for assessment are found, for example, in Leuwer, M, et al.: Checkliste Interdisziplinäre Intensivmedizin (Checklist for Interdisciplinary Intensive Medicine), Thieme Verlag Stuttgart, 1999.

In one particularly preferred embodiment, the daily dose of selenium amounts to at least 0.5 mg, preferably 1 mg, and the daily dose of zinc amounts to at least 10 mg, preferably at least 30 mg.

In a further preferred embodiment, administration of the composition according to the invention is done over at least three days, with both the above-mentioned daily dose of zinc and of selenium, whereby administration over at least five days is particularly preferred.

Preferably, the composition according to the invention is diluted with a compatible infusion solution before being administered. For example, in this way, 10 ml of the composition, corresponding to a daily dose, can be administered in at least 250 ml of a compatible infusion solution. This daily dose is preferably administered over a period of approximately 2 to 3 hours.

The composition according to the invention is preferably used for the nutrition of intensive care patients, particularly of sepsis patients. It has been seen that the mortality rate for sepsis patients can be noticeably lowered with the help of the composition according to the invention. At the same time, it is particularly significant that the selenium content of the composition is higher than in the state of the art.

Requirements for the manufacture of infusion solutions are described, for example, in European Pharmacopoeia, 4th Edition, Supplement 4.6, published by EDQM, 2003; page 3933.

Selenium

Pharmacodynamics

Mode of Action and Dose-Effect Relationship

Selenium is important for the activity of a number of enzymes. Until now, around 20 selenium proteins have been identified. Among the most important selenium-dependent enzymes that have been demonstrated in humans until now are: four glutathione peroxidases (cytosolic GSH-Px, plasma GSH-Px, gastrointestinal GSH-Px, phospholipid hydroperoxide GSH-Px), thioredoxin reductase (TR), the deiodinases and a selenium bonding protein found in plasma, selenoprotein P. Selenium is present in all selenium proteins as the amino acid selenocysteine.

In 1973, selenium was proven to be a constituent of glutathione peroxidase, therefore providing critical proof of the essential nature of this trace element. Meanwhile, glutathione peroxidase has been found in all mammal tissues in which oxidative processes occur. Through the catalysis of $H_2O_2$ to $H_2O$ (a) and of hydroperoxides to corresponding alcohols (b), the enzyme has a protective function against resultant products of reactive oxygen compounds and is consequently involved in the lipid peroxide protection of the organism.

$$H_2O_2 + 2GSH \rightarrow 2H_2O + GSSG \quad (a)$$

$$ROOH + 2GSH \rightarrow ROH + H_2O + GSSG \quad (b)$$

In cellular or sub-cellular model systems, it has been shown that the integrity of cellular and sub-cellular membranes is critically dependent upon the intactness of the glutathione peroxidase system. Consequently, selenium, as a constituent of glutathione peroxidase, can lower the lipid peroxidation rate and the membrane damages resulting from this as described, and furthermore, prevent genetic damage, mutations and, finally, the death of the cell.

Glutathione peroxidase, which contains selenium, furthermore influences the leukotriene, thromboxane and prostacyclin metabolism and is therefore significant for inflammatory processes.

In the form of sodium selenite, selenium has a further function, in addition to that of a selenium supplier: sodium selenite changes into selenous acid under hypoxic-acidotic conditions, and is consequently able to oxidise organic oxyl and hydroxyl radicals into ROOH or HOOH. Therefore, free radicals can be bound, enzyme-independently and spontaneously. This explains the effectiveness of sodium selenite, particularly in the early stages of sepsis. It is not to be expected that the synthesis of selenoproteins progresses optimally in patients in post-aggression metabolism. Consequently, a rise in glutathione peroxidase also cannot be observed until the third day of the selenium therapy, but nevertheless, the effectiveness of sodium selenite already begins on the first day.

Up to 70% of the plasma selenium is bound to selenoprotein P, a protein whose function has not been clearly explained yet. There are, however, explicit studies that, first, identify selenoprotein P as an extra-cellular antioxidant with a phospholipid-hydroperoxide-glutathione peroxidase function, and that, second, indicate that selenoprotein P apparently exercises a transport function. It is known that selenoprotein P can bond 35 mercury-selenium complexes (each with 100 mercury-selenium molecules) and excrete them via the urine.

The conversion of the thyroid hormone tetra-iodothyronine (T4) to biologically active triiodothyronine ($T_3$) is the job of the type I and type II deiodinase enzymes. In a number of studies, it could be shown that the type-I deiodinase that is found in the liver, kidney and thyroid is a selenoprotein that contains one atom of selenium per molecule in its active centre. This enzyme catalyses both the 5' and the 5-monodeiodinase and consequently forms both $T_3$ and $rT_3$. It generates 80% of the $T_3$ found in plasma. Type-II deiodinase, likewise a selenoprotein, is primarily found in the brain, in brown fat tissue and in the placenta, where it forms thyroxine $T_3$. The third deiodinase (type III) catalyses 5-monodeiodination, i.e., only $rT_3$ is formed by this enzyme. With this mechanism, by means of increased formation of $rT_3$, the metabolism can be curbed in case of hunger or serious illness, for example (low-$T_3$ syndrome). This enzyme is also described as a selenium-containing protein.

Furthermore, selenium plays a significant role in the immune defence. Animal experiments indicate that appropriate selenium doses have a positive influence on the immune system. By administering selenium, increased antibody formation, increased proliferation rates of the T and B lymphocytes and increased cytotoxicity of the T-lymphocytes and natural killer cells are achieved. In humans, administration of 200 µg of selenium a day for eight weeks increases the formation of the interleukin-2 receptor, the lymphocyte proliferation and the cell-destroying effect of the T-lymphocytes and natural killer cells (Kiremidjian-Schumacher et al. 2000, 1994, Roy et al. 1994). In humans, supplementation of 200 µg of selenium daily as sodium selenite led to a significant increase in natural killer cells within three weeks. Furthermore, by enriching table salt with 15 ppm of sodium selenite in a group of 20,847 test persons for five years, the incidence of primary liver cell cancer was reduced by 40% (versus the control of 109,624).

Selenium is also involved in the detoxification of heavy metals, such as cadmium, mercury, lead and arsenic. One mechanism consists of the formation of biologically inactive selenides, which prevents the bonding of mercury and cadmium to essential proteins.

Toxicology and Side-Effects

The $LD_{50}$ level was determined for sodium selenite on several experimental animals. After intravenous administration, the $LD_{50}$ level for mice was 2.2 mg of selenium/kg BW, for rats 5.7 mg/kg BW and for rabbits 0.9 mg/kg BW. After peroral administration, $LD_{50}$ was determined to be 2.25 mg/kg BW for rabbits, 2.3 mg/kg BW for guinea pigs and 3.2-3.5 mg/kg BW for mice.

Teratogenic and embryotoxic effects of selenium could be demonstrated in the experiment with animals.

Most of the studies on the effect of selenium compounds on tumours generated in animal experiments show an inhibitory effect of selenium compounds on tumour growth.

Acute toxicity for sodium selenite (various experimental animals) is 1-5 mg of selenium per kg BW; chronic toxicity is at 3-7 mg of selenium/day. The first symptoms of poisoning manifest themselves at 1.05 mg of selenium/l whole blood. Acute symptoms are increased sweating, vomiting, muscle spasms, cardiac arrhythmias; chronic symptoms are hair loss, brittle fingernails, skin changes, disturbances in the nervous system. In most cases, the symptoms are reversible and disappear within one to two weeks.

Acute selenium intoxications in humans are rarely described and can be attributed to the action of selenium dusts or hydrogen selenide in most cases.

For example, acute selenium poisoning was observed in two children who had drunk from a weapon-cleaning agent that contained approximately 1.8% selenous acid. In this manner, the children had ingested 10-15 ml of the agent, corresponding to roughly 110 mg=110,000 µg selenium, and died as a result. Chronic selenium poisonings in humans are primarily seen in areas with extremely high selenium content in the soils. Selenium ingestion in these areas is estimated at 3-7 mg of selenium a day.

In a report on a case of chronic poisoning with sodium selenite, the case of a 62-year-old man was described, who had taken 2 mg of sodium selenite, corresponding to 900 µg of selenium, daily for more than two years. A garlicky breath was detected. His fingernails were thickened and brittle, but grew normally again after the selenium intake was discontinued. Furthermore, the case of a 57-year-old woman was described, who had ingested approximately 27 mg of selenium a day in the form of sodium selenite for approximately two months, and who suffered from lassitude, nausea, vomiting, depression, bad breath, hair loss and nails that fell off. The poisoning symptoms were possibly moderated by the simultaneous ingestion of vitamin C. Four persons ingested 2 mg of selenium a day in the form of sodium selenite for 20-40 days, which did not result in any indications of selenium poisoning. After one year of peroral administration of 50 µg of selenium as sodium selenite per kg of bodyweight over one year, likewise no symptoms of selenium poisoning were observed in patients with neuronal ceroid lipofuscinosis.

Selenium poisonings are associated with increased selenium concentrations in the blood and urine. In humans, symptoms can appear from a selenium content of 1000 µg/l of whole blood.

Regarding long-term use (longer than three months), a dosage of up to 500 µg of selenium a day, or, in the form of inorganic salts such as sodium selenite, up to 550 µg of selenium, is seen as harmless. More recent recommendations are for at most 50 µg of selenium/kg BW (3500 µg/70 kg BW) as a single oral dose or at most 5 µg of selenium/kg BW (350 µg/70 kg BW) for long-term use. The currently valid WHO recommendation (1996) for the maximum safe ingestion over a longer time frame is 400 µg of selenium a day. This represents a compromise, which incorporates the differences, but that is only valid for healthy humans without selenium deficiency symptoms and without more serious stressful situations. People with very low selenium levels, consuming illnesses, chronic inflammations or infections or illnesses that are associated with surplus radical production, are not taken into account here and must be considered separately. The necessary, and therefore also tolerable, dosages are very much higher here.

Pharmacokinetics

Distribution and Metabolism

The absorption of selenium depends on its chemical bonding form and the composition of the nourishment. In meat, fish, eggs, plants and yeast, selenium is bonded to amino acids (selenomethionine and selenocysteine) and is predominantly absorbed in the small intestine by means of the active amino acids transport mechanism. Selenomethionine must be converted in several steps before it can be incorporated into selenoproteins. In intermediate metabolism, it competes with methionine and is therefore also non-specifically integrated into other proteins, particularly albumin (Waschulewski and Sunde 1988), as a result of which it is largely no longer available for the selenoproteins. In contrast, sodium selenite passes the intestinal mucosa via passive diffusion. The resorption rate amounts to between 44% and 80%. After oral administration of 1 mg of sodium selenite, several studies consistently showed absorption of an average portion of 62±14%.

In the blood, selenite is primarily absorbed by the erythrocytes. Hydrogen selenide serves as the central selenium pool for excretion and for systematic incorporation into selenoproteins. In this reduced form, selenium is bonded to plasma proteins and transported to the liver and other organs. The secondary plasmatic transport starting from the liver into the glutathione peroxidase-synthesising target tissue probably takes place in the form of a selenocysteine-containing P-selenoprotein. Finally, a selenocysteinyl-tRNA is formed, in which first a serinyl-tRNA is phosphorylated and then the selenium is incorporated in place of the sulphur in exchange for the phosphate group. The incorporation of selenocysteine into selenoproteins is a highly-specific process, and takes place at a defined position of the amino acid sequence with the help of selenocysteinyl-tRNA on the UGA codon of the m-RNA. The progress of the selenoprotein biosynthesis has been almost explained, both for prokaryonts and for eukaryonts. Surplus hydrogen selenide is metabolised via methylselenol and dimethylselenide into the trimethyl selenium ion, the primary excretory product.

The selenium content in the blood varies greatly, and is directly correlated with selenium absorption from the nourishment, whereby the highest levels are measured in the thrombocytes. But even in the erythrocytes, the amounts of selenium and the selenium-containing enzyme glutathione peroxidase are higher than in the serum. Because of the widely varying selenium concentrations in the blood, establishing normal values is problematic. Some authors quote a plasma level of from 40-190 µg/l. According to more recent results, selenium concentrations measured in humans are often 90-130 µg/l in whole blood and 75-120 µg/l in the serum. When there is a selenium concentration of up to approximately 160 µg/l in the whole blood, there is a close correlation between the selenium levels and the activity of the glutathione peroxidase in the erythrocytes. In the interest of maximum activity of the glutathione peroxidase and therefore sufficient protection against oxidative damages, a sufficiently high selenium content in the blood should be striven for. If sufficient selenium absorption through the food is not given, it is possible to supplement, for example, with sodium selenite. This particularly applies in case of clinically verified selenium deficiency.

The total amount of selenium in the human body is between 4 mg and 20 mg. In the human body, the thyroid, liver and kidneys hold the highest concentrations of selenium.

Excretion

The excretion of selenium in humans takes place via the faeces, urine or the lungs, depending on the dose applied. The excretion path depends on the selenium absorption and the selenium status. 50-70% of the selenium taken in with food leaves the organism renally. The urinary concentrations analysed in Europe are less than 30-40 µg of selenium/l. As the selenium absorption increases, the selenium excretion more clearly moves from the faeces to the urine, a fact that underlines the role of the kidney in the homeostatic regulation of the selenium balance. After the amount of selenium that exceeds the needs is absorbed, trimethyl selenonium becomes a major urinary metabolite.

A further detoxification metabolite of selenium is dimethylselenide, which is excreted in the breath. Excretion through the breath and skin is to be neglected under physiological conditions. Only when very high or toxic doses are administered is garlicky-smelling dimethylselenide additionally exhaled in the breath.

Excretion of selenium after intravenous or oral administration passes through three phases. With oral administration of 10 µg in the form of [$^{75}$Se] sodium selenite, 14-20% of the absorbed dose of selenium was excreted through the urine in the first two weeks, while practically no excretion through the lungs or skin could be detected. The total body retention of selenium decreased in three phases, with a half-life of 0.7-1.2 days in the $1^{st}$ phase, 7-11 days in the $2^{nd}$ phase and 96-144 days in the $3^{rd}$ phase. The selenium concentration fell in the liver, heart and plasma more rapidly than in the skeletal muscles or bones.

From an intravenously administered dose of [$^{75}$Se] sodium selenite, 12% was excreted in the first 24 hours. An additional 40% was eliminated with a biological half-life of 20 days. The half-life of the third phase was established at 115 days.

In a direct comparison of oral and intravenous administration of a physiological dose of [$^{74}$Se] sodium selenite, after intravenous administration of 82 µg of selenium in the form of sodium selenite, 18% of the dose was excreted in the first 24 hours, after peroral administration, 12% of the absorbed dose, together with metabolically-exchanged body selenium, was excreted through the urine. Accordingly, excretion progressed in the same way for both types of application. Sodium selenite applied orally and parenterally is comparable in the case of healthy test persons.

Zinc

Pharmacodynamics

Mode of Action and Dose-Effect Relationship

Zinc, the most important trace element quantitatively, is essential for the function as catalysts and regulator of more than 200 enzymes. Zinc metalloenzymes are found in 6 enzyme classes (oxidoreductases, transferases, hydrolases, lyases, isomerases, ligases) and therefore engage in all metabolic processes (proteins, carbohydrates, fats, nucleic acids, etc.).

For example, in the metabolism of proteins and nucleic acids, zinc fulfils numerous tasks, such as the stabilisation of the structure of DNA, RNA and ribosomes or as a constituent of enzymes key to nucleic acid synthesis (e.g., DNA polymerases). In addition, there are numerous physiologically-relevant interactions between zinc and various hormones (e.g., testosterone, adrenal corticoids, insulin, growth hormone), whereby production, storage and secretion and hormone receptor interactions can all be involved.

Zinc also plays a role in maintaining the structure and function of biomembranes. It is indispensable for fat metabolism, the function of the sensory organs (perception of taste) and maintenance of the immune functions. In pharmacological concentrations, zinc has an anti-oxidative effect on isolated cell systems (superoxide dismutase).

Zinc takes on an essential role in healing wounds, growth and in the framework of reproduction. The reason for this is the above-mentioned effect in nucleic metabolism. Furthermore, a satisfactory zinc level is important for storing insulin and the promotion of a positive N balance.

Heavy losses of zinc particularly occur when there is surgery in the intestinal area and during gastroenterologic illnesses with intestinal fistulas. Zinc deficiency has been observed during parenteral nutrition, treatment with chelating agents and extensive burns, among other situations.

Corresponding to zinc's roles in metabolism, zinc deficiency syndromes are manifold:

General symptoms: cessation of growth (children through bone growth depressions and reduced incorporation of amino acids into the musculature), weight loss (adults and children) up to cachexia in spite of a sufficient supply of amino acids and energy, impaired wound healing, loss of appetite with interference with the sense of taste, delayed development of the gonads, reduced glucose tolerance and an increase in the free fatty acids in the blood.

Gastrointestinal tract: therapy-resistant diarrhoeas (often as the first symptom), post-operative persistent intestinal atony.

Skin and mucous membranes: dermatitis that afflicts the surroundings of all body openings, alopecia areata, arrested growth of the nails (Beau's lines), parakeratoses and inflammatory changes of all mucous membranes.

Central nervous system: confusion, apathy, depressive mood, restlessness, testiness, agitation and photophobia.

Reproduction: premature births, deformities (mutagen, teratogen).

Plasma: hypozincemia (2-4 μmol/l, concentration declines, such as are not observed in stressful situations), hypoproteinemia, reduced activity of the alkaline phosphatases, degradation of the short-lived plasma proteins such as albumin, transferrin and prealbumin.

Immune system: depression of the cellular immunity (T-lymphocytes) facilitates germ invasion via the skin and mucous membranes, often leading to septicemias.

Urine: in spite of hypozincemia, increased zinc excretion in the urine, particularly when there are septic and catabolic conditions.

Acrodermatitis enteropathica: autosomal-recessive, impaired resorption.

The recommendation for an enteral zinc supply is indicated at 10 mg/d for men and 7 mg/d for women. Increased requirements exist during the growth period and in the reproductive phase, as well as during pregnancy and lactation. When there are larger gastrointestinal fluid losses, longer-lasting intestinal diseases or during treatment with D-penicillamine, as well as after persistent catabolic conditions, 3 μmol/kg (10-15 mg) should be administered.

With parenteral nutrition, the administered zinc is approximately 5 mg, and in the case of larger intestinal losses, one assumes an increase in the requirement of approximately 2 mg/d. Intravenous administration can also be calculated with 1 μmol/kg BW/d. The higher requirements in case of larger gastrointestinal fluid losses or during treatment with complexing agents should be allowed for by administering 3 μmol/kg BW/d. The Deutsche Arbeitsgemeinschaft für künstliche Ernährung (DAKE, German Consortium for Artificial Nutrition) and the Deutsche Gesellschaft für Ernahrungsmedizin (DEGM, German Society for Nutrition Medicine) cite 1.4-4.9 mg/d as the recommendation for parenteral nutrition.

Toxicology and Side-Effects

Zinc has low toxicity, with the toxic range not starting until quantities in the grams.

Acutely toxic effects of zinc essentially lead to gastrointestinal symptoms. They usually arise as a result of the consumption of acidic foods/drinks that were held in zinc-coated repositories.

Zink ingested per os has local and systemic poisonous actions. With the action of high concentrations, the local side effects are emphasised. The gastrointestinal events are based on a local corrosive effect (chloride>sulphate>acetate).

1 to 2 g of $ZnSO_4$ (225 to 450 mg zinc) per os result in vomiting, which offers a certain protection against resorptive poisoning. 5 g of $ZnSO_4$ or 3 to 5 g of $ZnCl_2$ (strong caustic) are considered deadly for adults.

Inadvertent intravenous infusion of a total of 7.4 g of zinc (as sulphate) within 60 hours ended with the death of a 72-year-old man after 47 days of non-specific symptoms with autoptically verified necrosis of the renal tubule and toxic liver damage.

The inadvertent intravenous infusion of 1.5 g of zinc over 60 hours ended fatally for a woman. She developed high blood pressure, pulmonary oedema, vomiting, jaundice and oliguria with kidney damage that manifested as necropsy.

A 16-year old boy who ingested 12 g of elementary zinc/d for 2 days developed recklessness, lethargy and dysgraphia, accompanied by an increased level of zinc in the blood, increased serum amylase and lipase activity, presumably as a result of the effect of the zinc on the pancreas function.

The toxicity of zinc when administered repeatedly is essentially identified by a copper deficiency and leads to hypochromic anaemia.

In another case, 150 mg of zinc a day over 2 years led to a copper deficiency, which was expressed as microcytic anaemia, neutropenia and lowered plasma levels of copper and ceruloplasmin.

In a 13-month old girl who had received 16 mg of zinc (as gluconate) a day prophylactically from the sixth month of life and, from one year, 24 mg of zinc a day, chronic zinc poisoning developed, with pronounced symptoms of copper deficiency.

20 healthy young men who received 160 mg of zinc/d for 5 weeks had normal levels of total cholesterol, triglycerides and LDL cholesterol. The HDL cholesterol level was significantly reduced, however, but normalised again 7 weeks after the treatment. In healthy young women, zinc supplementation with 100 mg daily for 8 weeks had no effect on the blood lipid levels, however.

After ingesting 220 mg of zinc sulphate twice a day for one week for acne treatment, a 15-year-old girl developed gastritis with hemorrhagic erosions, which healed spontaneously after the zinc preparation was discontinued.

Seen collectively, relatively high zinc doses per os are also well-tolerated over longer periods. Because of the metabolic interactions of zinc with copper, iron, calcium and cadmium, however, it is not possible to indicate the highest harmless dose of zinc. And even a moderately increased dose, as is customary in substitution treatment and possible with self-medication, can cause a (latent) copper deficiency, impair the immune function and—possibly—have an adverse effect on the lipoprotein profile.

Pharmacokinetics

Distribution and Metabolism

Zinc resorption occurs almost exclusively from the small intestine, both through passive diffusion and through active transport (cysteine-rich intestinal protein).

Homeostatic regulation of zinc resorption functions only when the mucous membrane is intact. Resorption is presumably controlled by interaction between two zinc-bonding proteins of the small intestine mucosa, first the "cysteine-rich intestinal protein" (CRIP), the zinc carrier for transport over the mucosa cell, and second, metallothionein, whose synthesis (in contrast to CRIP synthesis) is induced by excess zinc. In this way, excess zinc can be excluded from the resorption, to a certain extent.

Relatively more is resorbed from low-zinc nourishment than from high-zinc nourishment. There seems to be no specific storage location for zinc. This is why a dramatic reduction in the alimentary introduction rapidly results in a deficiency.

The resorption rate depends on the requirements and availability. In animal experimentation and with healthy humans, it was between less than 10 and more than 90%. Under physiological conditions, roughly 20-30% are resorbed from the nourishment.

Zinc resorption is particularly inhibited by phytate (inositol hexaphosphate), which is contained in grains in large amounts (Zn-phytate or not very easily soluble Zn—Ca phytate complexes). Furthermore, a low protein content and, to a less extent, a high fibre content in the nourishment have a negative influence on the zinc resorption. Iron, copper and calcium likewise inhibit the resorption of zinc, and vice versa: this is true for pharmacological doses (mineral compound preparations), but presumably not for the amounts naturally occurring in foods.

Zinc resorption is promoted by chelating agents such as EDTA and certain amino acids, which form complexes with zinc (histidine, tryptophan, prolin, lysine, glycine, cysteine), ascorbic acid and prostaglandin E2. Resorption is increased by picolinic acid, which is created from tryptophan and is secreted with the pancreatic juice, as well as by citrate, cysteine and glutamine.

The resorbed zinc is transported to the liver with the portal vein blood. With intravenous injection, it disappears from the blood into the liver, with a half-life of five minutes. The absorption of zinc in the cells takes place in competition with iron and calcium.

half-life of 250 to 500 days into the intestines (primarily in the small intestine), chiefly with the pancreatic juice and with the bile, and additionally with saliva, gastric juice and via the intestinal epithelium. It is also present to some extent in the bile as metallothionein. This excreted zinc can be reabsorbed and can enter into an enteropancreatic or enterohepatic circulation.

Physiological zinc losses through faeces, urine and skin amount to 1.4 mg/d in men and 1 mg/d in women. In cases of liver disease or serious injuries or burns, 1 to 4 mg/d are excreted via the urine. Pathological zinc losses arise when there is chronic bleeding (e.g., schistosomiasis, hook worm infections), fistulas (e.g., Morbus Crohn) or diarrhoea. Increased zinc excretion in the urine also occurs with extensive burns, injuries, hyperalimentation, liver cirrhosis, acute pancreatitis, infections, chronic kidney diseases, sickle cell anaemia, aminoaciduria in light of total parenteral nutrition, hypertonia treatment with thiazide diuretics and cancer treatment with cisplatin.

The following examples explain the invention.

State-of-the-Art Administration Form and Administration Form According to the Present Invention in Comparison Medication: Preparation according to the invention or Tracutil® (comparison preparation)

Form of administration: Infusion solution

Composition: 1 ampoule with 10 ml of infusion solution contains the following medically effective constituents Comparison of the composition according to the invention with the Tracutil® composition known from the state of the art:

TABLE

Composition of the medication

| Constituent | Quantity in mg Tracutil® | Quantity in mg syntrace® plus | Trace element | Quantity in mg Tracutil® | Quantity in mg syntrace® plus |
|---|---|---|---|---|---|
| Chromium(III) chloride 6H$_2$O | 0.053 | | Chromium | 0.01 | |
| Sodium fluoride | 1.260 | | Fluorine | 0.57 | |
| Potassium iodide | 0.166 | | Iodine | 0.13 | |
| Copper(II) chloride 2H$_2$O | 2.046 | | Copper | 0.76 | |
| Manganese(II) chloride 4H$_2$O | 1.979 | | Manganese | 0.55 | |
| Sodium molybdate 2H$_2$O | 0.0242 | | Molybdenum | 0.01 | |
| Iron(II) chloride 4H$_2$O | 6.958 | — | Iron | 1.95 | — |
| Sodium selenite 5H$_2$O | 0.0789 | 3.331 | Selenium | 0.02 | 1.00 |
| Zinc chloride | 6.815 | 62.542 | Zinc | 3.27 | 30.00 |
| Other constituents: | Hydrochloric acid, water for injection purposes | | | | |

The physiological serum concentration is 15.2±1.5 μmol/l, whereby this decreases as the age increases. For patients over 60 years of age, 11 μmol/l is a normal figure.

In keeping with its function, zinc is further distributed to all tissue. After parenteral administration, zinc also temporarily reaches considerable concentrations in the brain. In humans, the concentration in the cerebral spinal fluid accounts for a tenth of the plasma concentration. With zinc deficiency, the zinc concentration in the brain does not fall, and can, in fact, even increase. Zinc is specifically concentrated within the central nervous system, particularly in the nerve endings of the hippocampus, cortex and corpus pineale.

The amount of zinc held in the body is 20-30 mmol (1.5-2.5 g).

Excretion

90% of the zinc is excreted through the faeces, with the rest being renally excreted. In humans, three-fourths of the resorbed or parenterally administered zinc is excreted with a In addition to the increased concentration of selenium and zinc, divalent iron was left out of the present invention as a further change with respect to the intensive medicine patients, with the following justification. Iron deficiency is particularly caused by high losses of blood resulting from trauma or surgery, and must be balanced out by a blood transfusion in particular. Because bacteria need free iron to grow, the drop in the serum iron during infections and traumas as a result of an increase in the iron storage (ferritin) induced by cytokine represents a component in the non-specific immune defence. For these reasons, substitution of free iron should be refrained from in the acute phase and when there are infections. Moreover, from the summary of product characteristics for Tracutil® under the heading side-effects, it can be seen that in isolated cases, there have been reports of anaphylactic reactions to parenterally administered iron.

The following diagram shows the setup of this comparative trial.

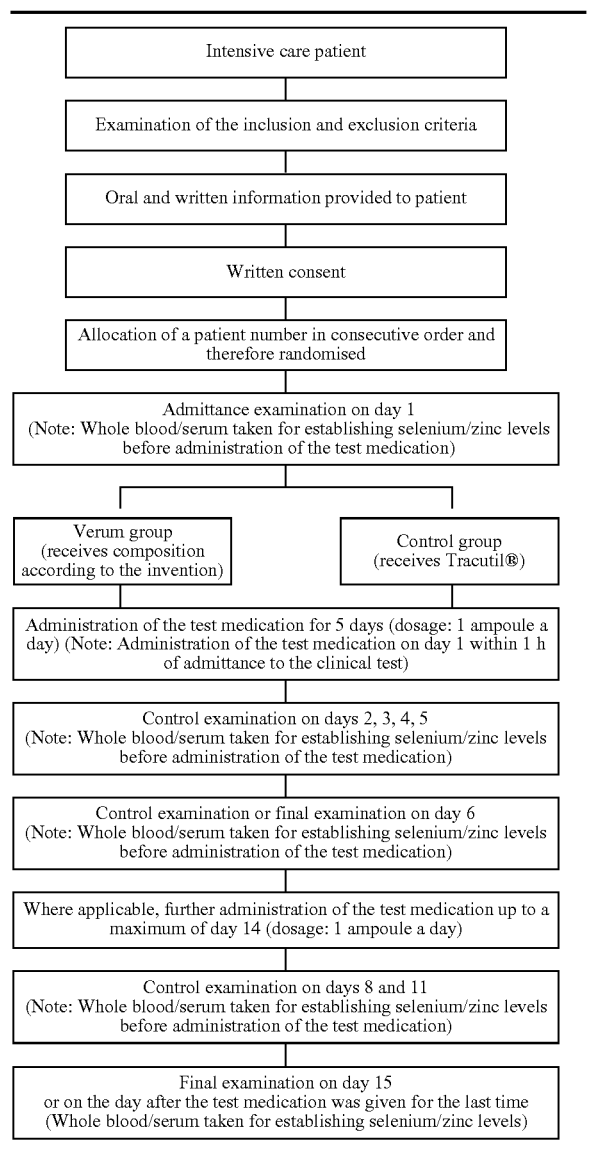

Dosage and Type of Application

For 5 days, a 10-ml ampoule of the medication is administered once a day. Infusion of the first ampoule must begin within the first hour after the patient is included in the clinical test. On the following days, further infusions must always be given before 12 noon, and always at the same time for each patient (±1 hour).

Example:
Sunday—2100: Admittance to the intensive care unit
Monday—1730: First administration of the medication (Day 1)
Tuesday—0800: Administration of the medication (Day 2)
Wednesday—0830: Administration of the medication (Day 3)
Thursday—0730: Administration of the medication (Day 4)
Friday—0800: Administration of the medication (Day 5)

If the intensive care patients are to be fed parenterally for longer than 5 days, the medication is administered up to Day 14 at the latest, according to the above plan.

The medication was diluted for application. 10 ml of the test medication (1 ampoule) was added to at least 250 ml of a compatible infusion solution and infused within 2 to 3 hours. The injection for the infusion solution should not be made until immediately before the application, and should be made under aseptic precautions.

To be used as the base solution are pure glucose solutions (5% to 70% glucose) or pure common salt solutions. The medication can also be added to a Ringer solution, whereby it must be noted that this is not permitted to be a Ringer-Lactate solution.

In principle, the medication can be applied via peripheral or central venous access. According to Elmadfa and Leitzmann 1990 and Semsroth 1994, the access is critically dependent on the indicated duration of the parenteral nutrition, on the pH level, on the osmolarity and on the chemical composition of the infusion solution. The catheter is set in a peripheral vein for short-term infusion therapy. If the parenteral supply of nutrition is to be given for more than three days, infusion is via central venous access. Patients were included who received parenteral nutrition for at least 5 days and, in addition, there had to be a mixing of the medication with another infusion solution; it is recommended that the application of the medicine takes place via central venous access. The decision on the type of access is left to the physician, however.

Substitution of the medication should take place only via a catheter through which no catecholamines are given, however. A further mixing of the medication with other substances to be infused should be avoided before the infusion. Under no circumstances should the medication be mixed with reduction agents such as vitamin C, for example, because here interactions, e.g., with sodium selenite, are possible and precipitation of elementary selenium cannot be ruled out. Elementary selenium is not soluble in an aqueous medium and is not bio-available. If administration of reducing substances is necessary, this should generally take place in a separate location and, if possible, at a different time from that of the administration of the medication.

Results of the Study of 52 Patients Receiving Parenteral Nutrition

In a study of 52 patients receiving parenteral nutrition, whereby the patients had haemorrhages, polytrauma/trauma and tumours, in the Vogtland-Klinikum Plauen GmbH, the trace element status of the patients was determined throughout the course of the therapy on the basis of routine medication and routine supplementation. Additional inclusion and exclusion criteria did not form a basis for selecting the patients.

The goal was to establish whether the routinely administered trace element substitution led to a satisfactory supply of trace elements. For this purpose, the serum and whole blood levels of the trace elements chromium, iron, fluorine, iodine, copper, manganese, molybdenum, selenium and zinc were determined daily, for a minimum of 3 and a maximum of 18 days.

The manganese, chromium, selenium and molybdenum content in serum and whole blood samples was determined by means of graphite furnace atomic absorption spectroscopy (graphite furnace AAS) according to the standard addition method (device type: Perkin Elmer Analyst 600).

The determination of iodine and fluorine was performed according to the standard addition method with ion-sensitive electrodes.

Throughout the above-mentioned observation period, the patients received the normal routine supplementation with the preparations Inzolen HK, Inzolen® sine NaCL, Selenase® and Unizink®, at various times and in various dosages. The trace elements cobalt, copper, manganese, selenium and zinc were administered by means of these preparations, in addition to the macro elements chloride, magnesium, potassium and sodium.

Corresponding to the previous routine, the Inzolen® administrations were made dependent on the daily determined serum potassium level, with the normal range being targeted. Zinc and selenium administration took place on the basis of experience in certain illness situations. The above-mentioned determination of the further macro element and trace element levels was only intended for retrospective observation of the trace element status, and was not included in the daily decision process for any supplementation.

The administered quantities of Inzolen HK, Inzolen® sine NaCL, Selenase® and Unizink®, as well as the resulting quantities of copper, manganese, selenium and zinc, can be seen in Table 3, Table 4 and Table 5.

TABLE 3

Administration of Unizink ®, Inzolen HK, Inzolen ® sine Na and selenase ®

| Preparation | Number of substituted patients | Range in ml | Total average administration in ml | Average administration in ml a day |
|---|---|---|---|---|
| Inzolen HK | 20 | 2-80 | 141 | 19 |
| Inzolen ® sine Na | 41 | 40-1900 | 489 | 52 |
| Selenase ® | 38 | 20-260 | 99 | 11 |
| Unizink ® | 21 | 60-450 | 227 | 18 |

TABLE 4

Total substituted quantity of zinc, copper, manganese and selenium by the preparations Unizink ®, Inzolen HK, Inzolen ® sine Na and selenase ®

| Element | Number of substituted patients | Range | Average | Median | Unit |
|---|---|---|---|---|---|
| Copper | 44 | 3.56–199.28 | 46.20 | 28.47 | mg |
| Manganese | 44 | 1.98–110.75 | 25.68 | 15.82 | mg |
| Selenium | 38 | 1,000.00–13,000.00 | 4,934.00 | 4,500.00 | µg |
| Zinc | 44 | 6.28–645.79 | 152.24 | 95.73 | Mg |

TABLE 5

Administration per day of zinc, copper, manganese and selenium by the preparations Unizink ®, Inzolen HK, Inzolen ® sine Na and selenase ®

| Element | Number of substituted patients | Range | Average | Median | Unit |
|---|---|---|---|---|---|
| Copper | 44 | 1.19–15.00 | 4.30 | 5.08 | mg |
| Manganese | 44 | 0.66–8.57 | 2.83 | 2.39 | mg |
| Selenium | 38 | 91.00–1,000.00 | 574.00 | 608.00 | µg |
| Zinc | 44 | 2.09–38.10 | 14.54 | 11.51 | mg |

The following reference ranges were the basis for the evaluation:

| | Chromium in nmol/l | Iron in µmol/l | Fluorine in µmol/l | Iodine in µmol/l | Copper in µmol/l |
|---|---|---|---|---|---|
| Serum | 0–19.23 | w 10.74–25.96 m 14.33–30.08 | 0.26–1.05 | 0.32–0.63 | 9.44–26.75 |
| Whole blood | 0–96.16 | 7,520.82–10,027.76 | — | 0.26–0.61 | 11.02–19.51 |

| | Manganese in nmol/l | Molybdenum in nmol/l | Selenium in µmol/l | Zinc in µmol/l |
|---|---|---|---|---|
| Serum | 5.46–54.61 | 0–10.42 | 1.28–1.71 | 9.18–19.88 |
| Whole blood | 127.42–191.12 | 10.42–104.23 | 1.53–2.05 | 61.17–114.70 |

In the statistical evaluation, the first step was to calculate, on a daily basis, how many patients (in percent) had trace element levels below, within or above the reference range. The second step was to establish what percent of the patients' trace element levels were below, within and above the reference range throughout the entire observation period (3-18 days).

Moreover, the behaviour curves of the trace element levels in the serum and whole blood of each patient were evaluated, whereby performance of further treatments/therapies (Op, CT, accompanying medication, etc.) was taken into consideration.

Selenium

Development of the selenium level of all patients, calculated in % relative to the reference range:

concluded from the results that in these patients long-term, high and continuous selenium substitution with 1000 µg/d is required.

Those few patients in whom the higher selenium concentrations in the serum indicated a selenium overdose always exhibited a selenium level in the whole blood that was within the reference range.

It could be observed that there was a reduced tendency towards infection when the selenium level was higher than when it was reduced.

Zinc

Development of the zinc level of all patients, calculated in % relative to the reference range:

| Selenium in serum | | Day | | | | | | | | | | | | | | | | | | |
|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | Ø |
| Below | % | 92 | 92 | 88 | 65 | 59 | 38 | 35 | 30 | 36 | 44 | 53 | 46 | 27 | 40 | 50 | 50 | 33 | 44 | 46 |
| Within | % | 2 | 8 | 8 | 27 | 24 | 35 | 30 | 26 | 36 | 39 | 24 | 8 | 27 | 20 | 10 | 10 | 33 | 33 | 20 |
| Above | % | 6 | 0 | 4 | 8 | 18 | 27 | 35 | 43 | 27 | 17 | 24 | 46 | 45 | 40 | 40 | 40 | 33 | 22 | 34 |
| Selenium in whole blood | | Day | | | | | | | | | | | | | | | | | | |
| | | 1 | 2 | 3 | 4 | 5 | 6 | 7 | 8 | 9 | 10 | 11 | 12 | 13 | 14 | 15 | 16 | 17 | 18 | Ø |
| Below | % | 96 | 98 | 94 | 89 | 76 | 59 | 65 | 70 | 64 | 75 | 72 | 79 | 77 | 83 | 75 | 82 | 90 | 60 | 80 |
| Within | % | 4 | 2 | 4 | 11 | 15 | 37 | 35 | 26 | 36 | 20 | 28 | 21 | 8 | 0 | 17 | 9 | 0 | 30 | 15 |
| Above | % | 0 | 0 | 2 | 0 | 9 | 4 | 0 | 4 | 0 | 5 | 0 | 0 | 15 | 17 | 8 | 9 | 10 | 10 | 5 |

Observations from the Behaviour Curves

Most of the patients exhibited a selenium deficiency throughout the entire observation period; this deficiency could be observed as a result of lowered selenium concentrations in both the serum and the whole blood.

| Zinc in serum | | Day | | | | | | | | | | | | | | | | | | |
|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | Ø |
| Below | % | 76 | 85 | 78 | 86 | 80 | 68 | 63 | 50 | 43 | 33 | 16 | 20 | 7 | 8 | 8 | 9 | 10 | 10 | 38 |
| Within | % | 20 | 13 | 22 | 14 | 17 | 29 | 38 | 50 | 52 | 62 | 68 | 73 | 79 | 92 | 92 | 91 | 80 | 80 | 49 |
| Above | % | 4 | 2 | 0 | 0 | 3 | 4 | 0 | 0 | 4 | 5 | 16 | 7 | 14 | 0 | 0 | 0 | 10 | 10 | 14 |
| Zinc in whole blood | | Day | | | | | | | | | | | | | | | | | | |
| | | 1 | 2 | 3 | 4 | 5 | 6 | 7 | 8 | 9 | 10 | 11 | 12 | 13 | 14 | 15 | 16 | 17 | 18 | Ø |
| Below | % | 6 | 18 | 12 | 14 | 17 | 7 | 8 | 4 | 0 | 0 | 0 | 7 | 7 | 0 | 0 | 0 | 0 | 0 | 5 |
| Within | % | 84 | 75 | 80 | 81 | 77 | 89 | 83 | 88 | 91 | 95 | 89 | 87 | 86 | 100 | 92 | 91 | 90 | 80 | 88 |
| Above | % | 10 | 8 | 8 | 5 | 6 | 4 | 8 | 8 | 9 | 5 | 11 | 7 | 7 | 0 | 8 | 9 | 10 | 20 | 7 |

Lowered selenium concentrations in the blood could particularly be measured in patients with multiple operations, sepsis, peritonitis and infections. If selenium was substituted in a higher dose (1000 µg/d) in these cases, the selenium levels in the serum rose directly, but sank again immediately when the selenium administration was ended.

Moreover, it was observed that the selenium level in the serum rose up into the reference range, but the whole blood levels rose only to just below the reference range. It was Observations from the Behaviour Curves The determination of the zinc level in the serum and in the whole blood revealed that this level was largely in the middle of the reference range throughout the entire course, and was therefore to be seen as normal.

What was conspicuous, however, was that a low zinc level in the serum did not signify an intracellular zinc deficiency, but that a high level in the serum was also not necessarily an indication of an intracellular excess.

In patients exhibiting a normal level of zinc in the whole blood and receiving administration of zinc, it could be observed that the zinc level in the serum was scarcely influenced, even when there was a high administration of zinc. The influence of the zinc dose on the zinc level in the whole blood was even less detectable. Normal levels in the whole blood also apparently represent a stable condition.

If the level of zinc in a patient's whole blood was lowered, however, administration of approximately 30 to 35 mg zinc/d was needed to normalise the level of zinc in the whole blood on a long-term basis. It was striking that patients with multiple operations and/or large wound areas, such as after traffic accidents, for example, required very high quantities of zinc. To prevent a deficiency, therefore, a corresponding high level of zinc substitution is absolutely necessary.

BIBLIOGRAPHY

Elmadfa and Leitzmann, C: Ernährung des Menschen (Human Nutrition). 2$^{nd}$ revised edition, Stuttgart: Eugen Ulmer Verlag, 1990: 385-392.

Gramm, H J, Kopf, A, Eyrich, K: Spurenelementsupplementierung im Rahmen langzeitiger parenteraler Ernährungstherapien (Trace Element Supplementation in the Framework of Long-term Parenteral Nutrition Therapies). Blätter, P, Gramm, H J (Publishers): Mineralstoffe und Spurenelemente in der Ernährung der Menschen (Mineral Compounds and Trace Elements in Human Nutrition). Blackwell Wissenschaft, Berlin, 1992: 34-44. ISBN 3-89412-115-7

Semsroth, M: Parenterale Ernährung (Parenteral Nutrition). Benzer, H, Burchardi, H, Larsen, R, et al. (Publishers): Intensivmedizin (Intensive Medicine, for corrected edition, Springer, Berlin, 1994: 120-150.

Deutsche Gesellschaft für Ernährung: Referenzwerte für die Nährstoffzufuhr (Reference Levels for the Administration of Nutrients/Deutsche Gesellschaft für Ernährung (DGE). (Konzeption und Entwicklung: Arbeitsgruppe: "Referenzwerte für die Nährstoffzufuhr") (Conception and Development: Workgroup: "Reference Levels for the Administration of Nutrients"). 1$^{st}$ edition, Frankfurt am Main: Umschau/Braus: 2000.

AMA American Medical Association, Department of Foods and Nutrition. Guidelines for Essential Trace Element Preparations for Parenteral Use. JAMA 214 (1979) 2051-2054.

National Advisory Group On Standards And Practice Guidelines For Parenteral Nutrition: Safe Practices for Parenteral Nutrition Formulations. Journal of Enteral and Parenteral Nutrition 22, 2 (1998) 49-66.

Hackl, J M: Leitfaden der parenteralen Ernährung (Guidelines for Parenteral Nutrition). Zuckschwerdt-Verlag Munich (1992).

Shenkin, A: Micronutrients and Antioxidants in Home Parenteral Nutrition. Clinical Nutrition 20. (Supplement 2) (2001) 47-50.

Rükgauer M, Kruse-Jarres, J D: Verteilung der Spurenelemente in den Fraktionen des Vollbluts (Trace Element Distribution in Whole Blood Fractions). 20. Mengen-und Spurenelemente, (20. Macro and Trace Elements) (2000) 137-145.

Heseker, H: Fluorid—Funktionen, Physiologie, Stoffwechsel, Empfehlungen und Versorgung in der Bundesrepublik Deutschland (Fluoride—Functions, Physiology, Metabolism, Recommendations and Supply in the Federal Republic of Germany). Ernährungs-Umschau (Nutrition Survey) 46 (1999) 8, 305-308.

Versieck J, Cornelis, R: Normal Levels of Trace Elements in Human Blood Plasma or Serum. Anal. Chim. Acta 116 (1980) 217-254.

The invention claimed is:

1. A method of nutrition comprising parenterally administering to a human a daily dose of 1 mg-2 mg of selenium and 30 mg-100 mg of zinc, wherein iron is not parenterally administered to the human.

2. The method of claim 1, wherein the human is an intensive care patient or a sepsis patient.

3. The method of claim 1, wherein the method further comprises administering trace elements selected from the group consisting of chromium, fluorine, copper, iodine, copper, manganese and molybdenum.

4. The method of claim 1, wherein the daily dose of 1 mg-2 mg of selenium and 30 mg-100 mg of zinc is administered for a period of at least 3 days.

5. The method of claim 4, wherein the daily dose of 1 mg-2 mg of selenium and 30 mg-100 mg of zinc is administered for a period of at least 5 days.

* * * * *